United States Patent [19]

Hoffmann et al.

[11] 4,279,636
[45] Jul. 21, 1981

[54] DICHLOROACETYLIMINO HERBICIDE ANTAGONISTS AS PLANT PROTECTION AGENTS

[75] Inventors: Otto L. Hoffmann, Shawnee; Joel L. Kirkpatrick, Overland Park, both of Kans.

[73] Assignee: Gulf Oil Corporation, Pittsburgh, Pa.

[21] Appl. No.: 137,670

[22] Filed: Apr. 4, 1980

Related U.S. Application Data

[62] Division of Ser. No. 946,975, Sep. 29, 1978, Pat. No. 4,237,302.

[51] Int. Cl.³ .......................................... A01N 43/82
[52] U.S. Cl. .......................................... 71/90
[58] Field of Search .................. 71/90; 548/139, 163, 548/195

[56] References Cited

U.S. PATENT DOCUMENTS

| 3,523,122 | 8/1970 | Capps | 260/306.7 T |
| 3,565,901 | 2/1971 | Cebalo | 260/299 |
| 4,021,224 | 6/1977 | Pallos et al. | 71/88 |
| 4,092,148 | 5/1978 | Cebalo | 71/90 |

FOREIGN PATENT DOCUMENTS

| 2218097 | 11/1972 | Fed. Rep. of Germany. | |
| 50-13814 | 5/1970 | Japan | 260/306.7 T |
| 49-6650 | 2/1974 | Japan | 71/90 |

OTHER PUBLICATIONS

L. Bambas, Five-Membered Heterocyclic Compounds with Nitrogen and Sulfur, (1952), Interscience Publishers, NY, pp. 103-104.

Primary Examiner—Donald G. Daus
Assistant Examiner—M. C. Eakin
Attorney, Agent, or Firm—Carl A. Cline

[57] ABSTRACT

New compounds which are herbicide antagonists that are useful for protection of plants from various herbicides are members of the group having the general structural formulas:

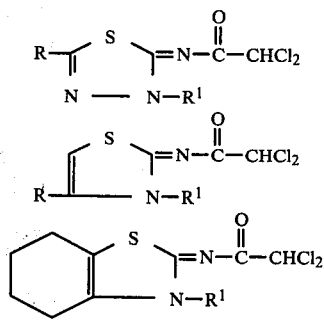

in which R is hydrogen or $C_1$ to $C_4$ alkyl, alkenyl or alkynyl, branched or straight chain, $R^1$ is $C_1$ to $C_3$ alkyl, alkenyl or alkynyl, branched or straight chain, with the total number of carbon atoms in R and $R^1$ being less than six, preferably less than four, on compounds with both R and $R^1$ substituents. The novel plant protection agents may be applied both to seeds and to the soil.

5 Claims, No Drawings

DICHLOROACETYLIMINO HERBICIDE ANTAGONISTS AS PLANT PROTECTION AGENTS

This is a division of application Ser. No. 946,975, filed Sept. 29, 1978, now U.S. Pat. No. 4,237,302.

DESCRIPTION OF THE INVENTION

Amides of dichloroacetic acid derived from a large number of amines are known to be useful as herbicide antagonists to protect plants from pre-emergent thiocarbamate herbicides, as disclosed in U.S. Pat. Nos. 4,021,224 and 4,033,756. Plant protecting antagonists have been used commercially in two ways, (1) by application to the crop seeds at, or prior to planting, so as to assure that antagonist is present when the seeds germinate and begin to grow, or (2) by application to the soil, so that if pre-emergent herbicide in the soil reaches the crop seeds, the antagonist will also be present and will protect the germinating and growing plants. The second method is not as controllable as the first method. Diffusion of the antagonist in the soil may be at a different rate from the diffusion rate of the herbicide and the difference may be dependent upon weather and soil type. Direct seed treatment is generally more effective and efficient with respect to the use of chemicals. However, application to the soil is very convenient and requires very little labor, because both antagonist and herbicide may be applied simultaneously.

In general, dichloroacetamides of amino-substituted heterocyclic compounds have not been shown to be able to completely eliminate injury to corn by a thiocarbamate herbicide such as EPTC applied at rates of 6 pounds or more per acre. For example, dichloroacetamides derived from thiazoleamines, oxazoleamines and thiadiazoleamines have not given sustained protection, either when applied to the seed or allowed to migrate through the soil. Amides derived from tetrahydrofurfurylamine, aminopicoline, aminochloropyridine, diaminopyridine and furfurylamine have been shown to give protection when used to treat corn seed. However, the dichloroacetamides derived from aminoheterocyclic compounds have not fared well as soil-applied antagonists. Amides derived from aliphatic amines such as diallylamine and diisopropylamine have given much better performance when applied to the soil. However, all soil-applied antagonists suffer from the lack of a lasting effect. Apparently the concentration of antagonist in the soil diminishes with time until the developing plants are unable to absorb enough to obtain the desired protection. Application of dichloroacetamides to the soil at higher rates to assure a lasting effect usually results in plant injury, as these compounds are phytotoxic at higher concentrations.

We have discovered a new class of plant-protecting antagonists which appear to give lasting protection against various herbicides at a variety of application rates, both when applied directly to crop seeds, and when applied to the soil. Although we do not wish to be limited by this theory, there are indications that these compounds are less phytotoxic than the dichloroacetamides and are more resistant to decomposition by soil fungi and bacteria. The new class of plant protecting antagonists, including all which are useful for either soil application or direct application to seeds are the compounds of the group having the general structural formulas:

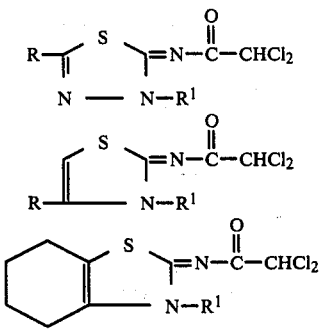

in which R is hydrogen or $C_1$ to $C_4$ alkyl, alkenyl or alkynyl, branched or straight chain and $R^1$ is $C_1$ to $C_3$ alkyl, alkenyl or alkynyl, branched or straight chain, with the total number of carbon atoms in R and $R^1$ being less than six and preferably less than four, on compounds with both R and $R^1$ substituents.

New compounds which are particularly outstanding for their ability to protect developing plants from various herbicides, either when applied to plant seed, or to the soil, are exemplified below:

| Compound No. | Structural Formula | M.P. (°C.) |
|---|---|---|
| 1 | (structure with S, =N–C(O)–CHCl$_2$, N—N–CH$_3$) | 95–97 |
| 2 | (structure with H$_3$C–, S, =N–C(O)–CHCl$_2$, N–CH$_3$) | 146–148 |
| 3 | (structure with H$_3$C–, S, =N–C(O)–CHCl$_2$, N—N–CH$_3$) | 89–91 |
| 4 | (structure with S, =N–C(O)–CHCl$_2$, N—N–C$_2$H$_5$) | Oil |
| 5 | (structure with H$_3$C–, S, =N–C(O)–CHCl$_2$, N—N–C$_2$H$_5$) | 91–93 |

The following new compounds are particularly outstanding as plant protectants when applied to the soil:

| Compound No. | Structural Formula | M.P. (°C.) |
|---|---|---|
| 6 | (structure with S, =N–C(O)–CHCl$_2$, N–CH$_3$) | 118–121 |
| 1 | (structure with S, =N–C(O)–CHCl$_2$, N—N–CH$_3$) | 95–97 |
| 2 | (structure with H$_3$C–, S, =N–C(O)–CHCl$_2$, N–CH$_3$) | 146–148 |

-continued

| Compound No. | Structural Formula | M.P. (°C.) |
|---|---|---|
| 3 | H₃C—[S,N ring]—N—CH₃ =N—C(O)—CHCl₂ | 89–91 |
| 4 | [S,N ring]—N—C₂H₅ =N—C(O)—CHCl₂ | oil |
| 5 | H₃C—[S,N ring]—N—C₂H₅ =N—C(O)—CHCl₂ | 91–93 |
| 7 | [S,N ring]—N—CH₂—C≡CH =N—C(O)—CHCl₂ | 91–93 |

Other new compounds which are outstanding for use as direct seed treating agents are the following:

| Compound No. | Structural Formula | M.P. (°C.) |
|---|---|---|
| 8 | cyclohexene-fused [S,N ring]—N—CH₃ =N—C(O)—CHCl₂ | 103–105 |
| 9 | CH₃—C(CH₃)=CH—[S,N ring]—N—CH₃ =N—C(O)—CHCl₂ | 118–121 |
| 1 | [S,N ring]—N—CH₃ =N—C(O)—CHCl₂ | 95–97 |
| 2 | H₃C—CH=[S,N ring]—N—CH₃ =N—C(O)—CHCl₂ | 146–148 |
| 4 | [S,N ring]—N—C₂H₅ =N—C(O)—CHCl₂ | oil |

The compounds numbered 1 and 4 are particularly outstanding for use in protecting rice from alachlor.

SYNTHESIS OF COMPOUNDS

Scheme 1 gives a generalized method of synthesis for this class of compounds.

SCHEME 1

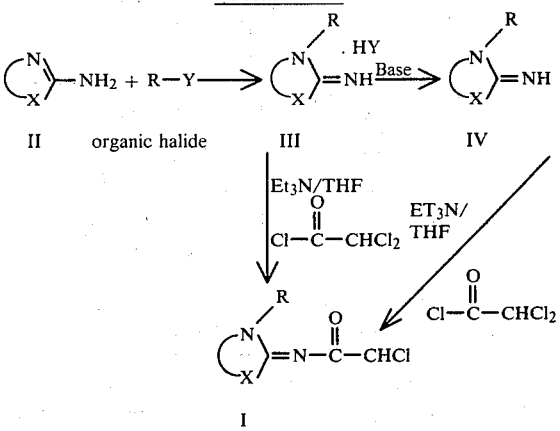

Scheme 2 gives the specific synthesis for compound No. 6, 2-dichloroacetylimino-3-methylthiazol-4-ine.

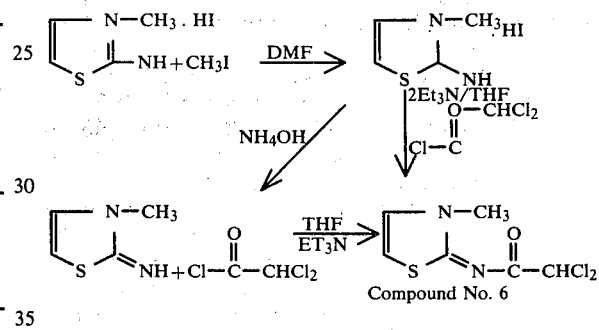

The compounds used as starting materials may be obtained from commercial sources or are readily prepared by means of published procedures. Suitable procedures appear, for example, in the following sources: Kubo, H.; Sato, R.; Hamura, I. and Ohi, T. J. Ag. Food Chem., v. 18 p. 60(1970) Lalezari, I. and Sharghi, V. J. Heter. Chem. v. 3 p. 336 (1966) Hurd, C. D. and Wehrmeister, H. L. J. Am. Chem. Soc. v. 71 p. 4007 (1949). Specific synthesis procedures are exemplified below for illustrative purposes.

Preparation of 2-imino-3-methylthiazol-4-ine hydroiodide

To a solution of 20 g (0.2 m) of 2-aminothiazole (Aldrich Chemical Co.) in DMF (dimethylformamide) (50 ml) was added 35 g (0.25 m) of methyl iodide and the solution stirred at room temperature for 72 hrs. Upon the addition of ethyl acetate, the product crystallized and was collected, giving 44 g, m.p. 185°–187° C.

Preparation of 2-dichloroacetylimino-3-methylthiazol-4-ine

To a suspension of 4.0 g (0.017 m) of 2-imino-3-methylthiazol-4-ine hydroiodide in THF (tetrahydrofuran) (100 m) was added 5 g of triethylamine. After stirring at room temperature for a few minutes, 2.0 g (0.018 m) of dichloroacetyl chloride was added and stirring was continued for an additional 4 hours. The precipitated salts were collected by filtration and washed with portions of THF, then the filtrate was concentrated to near dryness at reduced pressure. Water was added and the resulting mixture was extracted with ethyl acetate, which was removed at reduced pressure and the residue was then crystallized with ether. The product, 2-dichloroacetylimino-3-methylthiazol-4-ine, was collected and gave 2.0 g, M.P. 118°–131° C.

Use as Plant Protecting Antagonists

These antagonists can be useful for reducing the herbicidal injury to many crop plants. Examples of herbicides against which plants are protected include alachlor, butylate, cycloate, pebulate, N-chloroacetyl-N-(2,6-diethylphenyl)glycine ethyl ether, diallate, dicamba, dinitramine, N-[3[(1,1,1-trifluoromethylsulfonyl)amino]-4-methylphenyl] acetamide, EPTC, molinate, oxadiazon, perfluidone, propachlor, vernolate and CDEC. (Chemical composition and other information regarding the aforementioned herbicides may be obtained from the *Pesticide Manual* (issued by The British Crop Protection Council, Fifth Edition, January 1977). Examples of crops that are protected are rice, corn, barley, wheat, oats and grain sorghum.

These antagonists may be applied in many known ways: as seed treatments, as soil applied protectants, or by seed soaking. The seed treatments may be applied dry, as slurries, or as furrow sprays. The soil treatments may be made over the entire field or to small portions of the field. They may be applied as sprays, dusts or granules. The following examples are presented by way of illustration.

EXAMPLE 1

Soil Applied Plant Protectants

Method:

0.60 g chemical is ground with 4.0 ml of a surfactant mixture (composed of 3 parts Emulphor EL-300, 1 part kerosene and 1 part xylene). An aliquot containing 10.4 mg (2 lb/A) is obtained for antidote assay. This is put in 50 ml $H_2O$ and EPTC is added (41.6 mg or 8 lb/A). The mixture is applied to a 6 in. by 12 in. plastic flat containing soil seeded to 5 kernels of corn.

After three weeks the corn was scored as follows with a three digit code: 5-0-5. The first digit refers to the number of plants emerging. The second number refers to the number of plants distorted by EPTC and the third number refers to the height of the plants. Thus a result scored 5-5-1 would be indistinguishable from EPTC treated checks and a 5-0-5 would be like an untreated check on which there was neither herbicide nor protectant.

Results:

The chemical compounds numbered 1, 2 and 6 gave ratings of 5-0-5, indicating that complete protection was obtained at the application rates of the procedure described above.

EXAMPLE 2

Application of Protectants by Seed Treatment; Corn-EPTC

Method:

5.0 g corn seed is treated with the indicated amount (1/8%, ½% or 3% by wt.) of chemical in a 3-dram vial. Five small drops (1%) methanol is added and the vial is shaken 20 sec. in a Spex mixer. Five seeds are planted in greenhouse soil in a 6 in. × 12 in. plastic flat. 8 lb/A EPTC is applied directly over the seed in 50 ml. water. The seed is covered and the flat is watered.

Three weeks later the plants are scored as in Example 1.

Results:

Compounds which gave perfect scores (5-0-5) are as follows:

| Compound No. | Treatment rate in % by weight of seed | | |
|---|---|---|---|
| | ⅛% | ½% | 3% |
| 1 | 5-0-5 | 5-0-5 | |
| 2 | 5-0-5 | 5-0-5 | |
| 8 | | 5-0-5 | 5-0-5 |
| 9 | 5-0-5 | 5-0-5 | |

The compounds disclosed above were employed as plant-protecting agents, both by soil and seed treatment at various application rates, with various herbicides, according to the exemplified procedures. Perfect scores of 5-0-5 which were obtained are tabulated below.

| Compound Number | Type of Application and rate | Crop | Herbicide and rate | Remarks |
|---|---|---|---|---|
| 1 | 1–8 lb/A. on soil | corn | EPTC 8 lb/A. | (preferred use) |
| 1 | 2 lb/A. on soil | corn | vernolate 3 lb/A. | |
| 1 | 2 lb/A. on soil | corn | molinate 6 lb/A. | |
| 1 | 2 lb/A. on soil | corn | cycloate 4 lb/A. | |
| 1 | 2 lb/A. on soil | corn | ethiolate 3 lb/A. | |
| 1 | 2 lb/A. on soil | corn | ethyl N-2-chloroacetyl-N-(2,6-diethylphenyl) glycinate 4 lb/A. | |
| 1 | 2 lb/A. on soil | corn | CDEC 4 lb/A. ethyl 2-methyl-4-chlorophenoxythiolacetate | |
| 1 | 2 lb/A. on soil | corn | oxadiazon 4 lb/A. | |
| 1 | ½% w/w on seed | rice | alachlor 2 lb/A. | (preferred use) |
| 2 | 1–8 lb/A. on soil | corn | EPTC 8 lb/A. | |
| 2 | 2 lb/A. on soil | corn | vernolate 3 lb/A. | |
| 2 | 2 lb/A. on soil | corn | molinate 6 lb/A. | |
| 2 | 2 lb/A. on soil | corn | cycloate 1 lb/A. | |
| 2 | 2 lb/A. on soil | corn | ethiolate 3 lb/A. | |
| 2 | 2 lb/A. on soil | corn | diallate 4 lb/A. | |
| 3 | 1 lb/A. on soil | corn | EPTC 6 lb/A. | (antagonist and herbicide sprayed as mixture) |
| 4 | 1 lb/A. on soil | corn | EPTC 6 lb/A. | (antagonist and herbicide sprayed as mixture) |
| 5 | 1 lb/A. on soil | corn | EPTC 6 lb/A. | |
| 6 | ½ to 8 lb/A. on soil | corn | EPTC at 8 lb/A. | (antagonist and |

-continued

| Compound Number | Type of Application and rate | Crop | Herbicide and rate | Remarks |
|---|---|---|---|---|
| 6 | 2 lb/A. on soil | corn | vernolate 3 lb/A. | herbicide sprayed as mixture) (antagonsit and herbicide sprayed as mixture) |
| 6 | 2 lb/A. on soil | corn | molinate 6 lb/A. | (antagonist and herbicide sprayed as mixture) |
| 6 | 2 lb/A. on soil | corn | cycloate 4 lb/A. | (antagonist and herbicide sprayed as mixture) |
| 6 | 2 lb/A. on soil | corn | pebulate 2 lb/A. | (antagonist and herbicide sprayed as mixture) |
| 6 | 2 lb/A. on soil | corn | ethiolate 3 lb/A. | (antagonist and herbicide sprayed as mixture) |
| 6 | 2 lb/A. on soil | corn | CDEC 4 lb/A. | (antagonist and herbicide sprayed as mixture) |
| 6 | 2 lb/A. on soil | corn | diallate 4 lb/A. | (antagonist and herbicide sprayed as mixture) |
| 7 | 1 to 8 lb/A. on soil | corn | EPTC 8 lb/A. | (antagonist and herbicide sprayed as mixture) |
| 7 | 2 lb/A. on soil | corn | vernolate 3 lb/A. | (antagonist and herbicide sprayed as mixture) |
| 7 | 2 lb/A. on soil | corn | molinate 6 lb/A. | (antagonist and herbicide sprayed as mixture) |
| 7 | 2 lb/A. on soil | corn | cycloate 4 lb/A. | (antagonist and herbicide sprayed as mixture) |
| 7 | 2 lb/A. on soil | corn | pebulate 2 lb/A. | (antagonist and herbicide sprayed as mixture) |
| 7 | 2 lb/A. on soil | corn | ethiolate 3 lb/A. | (antagonist and herbicide sprayed as mixture) |
| 7 | 2 lb/A. on soil | barley | molinate 6 lb/A. | (antagonist and herbicide sprayed as mixture) |
| 7 | 2 lb/A. on soil | rice | molinate 6 lb/A. | (antagonist and herbicide sprayed as mixture) |
| 8 | 1% w/w on seed | corn | EPTC 8 lb/A. | (antagonist and herbicide sprayed as mixture) |
| 8 | 1% w/w on seed | corn | molinate 6 lb/A. | (antagonist and herbicide sprayed as mixture) |
| 8 | 1% w/w on seed | corn | cycloate 4 lb/A. | (antagonist and herbicide sprayed as mixture) |
| 8 | 1% w/w on seed | corn | alachlor 2 lb/A. | (antagonist and herbicide sprayed as mixture) |
| 8 | 1% w/w on seed | corn | ethiolate 3 lb/A. | (antagonist and herbicide sprayed as mixture) |
| 8 | 1% w/w on seed | corn | CDEC 4 lb/A. | (antagonist and herbicide sprayed as mixture) |
| 8 | 1% w/w on seed | corn | diallate 4 lb/A. | (antagonist and herbicide sprayed as mixture) |

The herbicide antagonists of this invention must be applied in an effective amount, sufficient to improve the resistance of the plants to pre-emergent herbicides. The skilled worker in the art will be able to determine what is an effective amount by examination of the data in the illustrative examples. It will be readily understood that application to seeds requires a smaller amount of antagonist. The use of excessive amounts is uneconomical and accomplishes nothing beneficial. However, accidental application of an excessive amount, as for instance by overlapping of sprayed areas does not result in reduction of the number of emerging plants or the appearance of pre-emergence herbicidal effects. The substantially nonphytotoxic character of these herbicide antagonists is unique and contrasts sharply with the characteristics of the dichloroacetamides. Compounds numbered 1, 2, 6 and 7, as shown in the foregoing table, gave perfect scores in protecting corn from EPTC even when applied to soil at rates as high as 8 lb. per acre.

The herbicide antagonists of this invention are effective against various types of pre-emergent herbicides. Commercial herbicides have been used in the illustrative examples so as to demonstrate practical utility. Thiocarbamates and dithiocarbamates are probably the most numerous and readily available of the commercial pre-emergent herbicides and these appear most often in the examples. However, it should be recognized that efficacy against a substituted oxadiazolinone (oxadiazon) and a chloroacetanilide (alachlor) are also demonstrated. It is not intended to limit the method of protecting crop plants to protection against only the herbicides of the illustrative examples.

We claim:

1. The method of protecting crop plants from herbicides which comprises applying to the crop seeds or to the soil in which the seeds are planted an effective amount, sufficient to improve the resistance of the crop plants to a pre-emergent herbicide of a compound having a structural formula selected from the following formulas,

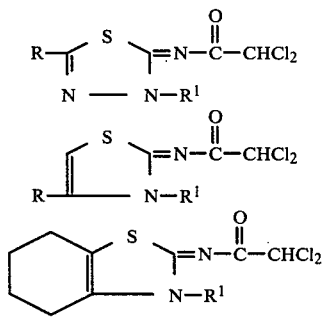

in which R is hydrogen or $C_1$ to $C_4$ alkyl, alkenyl or alkynyl, branched or straight chain and $R^1$ is $C_1$ to $C_3$ alkyl, alkenyl or alkynyl, branched or straight chain, with the total number of carbon atoms in R and $R^1$ being less than six when both R and $R^1$ substituents are present.

2. The method of protecting corn plants from a pre-emergent herbicide which comprises applying to the corn seeds or the soil in which the seeds are planted an effective amount of a herbicide antagonist compound which has the structural formula

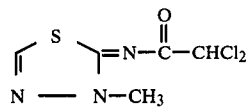

sufficient to increase the resistance of the corn plants to a pre-emergent herbicide.

3. The method of protecting rice plants from alachlor which comprises applying to the rice seeds or the soil in which the rice seeds are planted an effective amount of the compound which has the structural formula

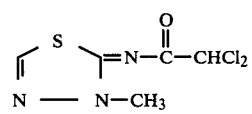

sufficient to improve the resistance of the rice plants to alachlor.

4. The method of protecting grain crops from a pre-emergent herbicide which comprises applying to the crop seeds or to the soil in which the crop seeds are planted an effective amount of the compound which has the structural formula

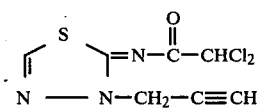

sufficient to improve the resistance of the crop plants to a pre-emergent herbicide.

5. The method of protecting rice plants from alachlor which comprises applying to the rice seeds or the soil in which the rice seeds are planted an effective amount of the compound which has the structural formula

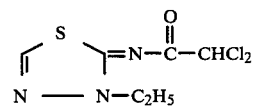

sufficient to improve the resistance of rice plants to alachlor.

* * * * *

UNITED STATES PATENT AND TRADEMARK OFFICE
CERTIFICATE OF CORRECTION

PATENT NO. : 4,279,636

DATED : July 21, 1981

INVENTOR(S) : Otto L. Hoffmann and Joel L. Kirkpatrick

It is certified that error appears in the above—identified patent and that said Letters Patent is hereby corrected as shown below:

Column 4, Scheme 1, lines 10-15, the formula should read (in part):

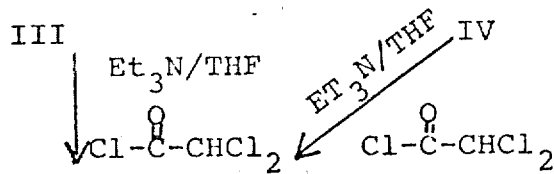

Column 4, Scheme 2, lines 23-26, the formula should read (in part):

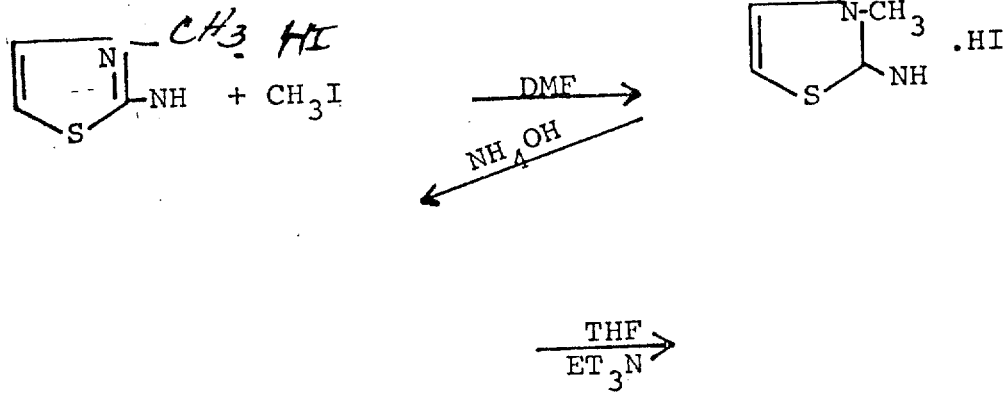

UNITED STATES PATENT AND TRADEMARK OFFICE
CERTIFICATE OF CORRECTION

PATENT NO. : 4,279,636

DATED : July 21, 1981

INVENTOR(S) : Otto L. Hoffmann and Joel L. Kirkpatrick

It is certified that error appears in the above—identified patent and that said Letters Patent is hereby corrected as shown below:

Column 6, Example 2, second table, 13th item, under the Herbicide and rate column, "cycloate 1b/A." should read "cycloate 4lb/A."

Signed and Sealed this

Twenty-third Day of March 1982

[SEAL]

Attest:

GERALD J. MOSSINGHOFF

Attesting Officer — Commissioner of Patents and Trademarks